US009369798B1

(12) United States Patent
Alderson et al.

(10) Patent No.: US 9,369,798 B1
(45) Date of Patent: Jun. 14, 2016

(54) INTERNAL DYNAMIC RANGE CONTROL IN AN ADAPTIVE NOISE CANCELLATION (ANC) SYSTEM

(71) Applicant: Cirrus Logic, Inc., Austin, TX (US)

(72) Inventors: Jeffrey Alderson, Austin, TX (US); Jon D. Hendrix, Wimberly, TX (US); Gautham Devendra Kamath, Austin, TX (US)

(73) Assignee: CIRRUS LOGIC, INC., Austin, TX (US)

( * ) Notice: Subject to any disclaimer, the term of this patent is extended or adjusted under 35 U.S.C. 154(b) by 356 days.

(21) Appl. No.: 13/794,979

(22) Filed: Mar. 12, 2013

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04B 15/00*** | (2006.01) |
| ***H04R 3/00*** | (2006.01) |

(52) U.S. Cl.
CPC ........ *H04R 3/002* (2013.01); *G10K 2210/3051* (2013.01)

(58) Field of Classification Search
CPC .................. G10K 11/1788; G10K 2210/3051; G10K 11/178; G10K 11/1784; G10K 2210/108; G10K 2210/1081; H04R 1/1083; H04R 3/002
USPC ........ 381/71.2, 72.1, 71.11, 71.12, 334, 94.7, 381/122
See application file for complete search history.

(56) References Cited

U.S. PATENT DOCUMENTS

| | | | |
|---|---|---|---|
| 4,020,567 | A | 5/1977 | Webster |
| 4,926,464 | A | 5/1990 | Schley-May |
| 4,998,241 | A | 3/1991 | Brox et al. |
| 5,018,202 | A | 5/1991 | Takahashi |
| 5,021,753 | A | 6/1991 | Chapman |
| 5,044,373 | A | 9/1991 | Northeved et al. |
| 5,117,401 | A | 5/1992 | Feintuch |
| 5,251,263 | A | 10/1993 | Andrea et al. |

(Continued)

FOREIGN PATENT DOCUMENTS

| | | | |
|---|---|---|---|
| DE | 102011013343 | A1 | 9/2012 |
| EP | 0412902 | A2 | 2/1991 |

(Continued)

OTHER PUBLICATIONS

U.S. Appl. No. 13/686,353, filed Nov. 27, 2012, Hendrix, et al.

(Continued)

*Primary Examiner* — Vivian Chin
*Assistant Examiner* — Douglas Suthers
(74) *Attorney, Agent, or Firm* — Mitch Harris, Atty at Law, LLC; Andrew M. Harris

(57) ABSTRACT

A personal audio device, such as a headphone, includes an adaptive noise canceling (ANC) circuit that adaptively generates an anti-noise signal using one or more microphone signals that measure the ambient audio. The anti-noise signal is combined with source audio to provide an output for a speaker. The anti-noise signal causes cancellation of ambient audio sounds that appear in the microphone signals. A processing circuit uses the reference microphone to generate the anti-noise signal using one or more adaptive filters. The processing circuit also includes low-pass filters that remove quantization noise images at the output of the adaptive filter to reduce the dynamic range required at the output of the adaptive filter.

24 Claims, 7 Drawing Sheets

(56) References Cited

U.S. PATENT DOCUMENTS 5,278,913 A 1/1994 Delfosse et al.
5,321,759 A 6/1994 Yuan
5,337,365 A 8/1994 Hamabe et al.
5,359,662 A 10/1994 Yuan et al.
5,377,276 A 12/1994 Terai et al.
5,386,477 A 1/1995 Popovich et al.
5,410,605 A 4/1995 Sawada et al.
5,425,105 A 6/1995 Lo et al.
5,445,517 A 8/1995 Kondou et al.
5,465,413 A 11/1995 Enge et al.
5,481,615 A 1/1996 Eatwell et al.
5,548,681 A 8/1996 Gleaves et al.
5,550,925 A 8/1996 Hori et al.
5,559,893 A 9/1996 Krokstad et al.
5,586,190 A 12/1996 Trantow et al.
5,640,450 A 6/1997 Watanabe
5,668,747 A 9/1997 Ohashi
5,687,075 A 11/1997 Stothers
5,696,831 A 12/1997 Inanaga et al.
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,852,667 A 12/1998 Pan et al.
5,909,498 A 6/1999 Smith
5,940,519 A 8/1999 Kuo
5,946,391 A 8/1999 Dragwidge et al.
5,991,418 A 11/1999 Kuo
6,041,126 A 3/2000 Terai et al.
6,118,878 A 9/2000 Jones
6,181,801 B1 1/2001 Puthuff et al.
6,219,427 B1 4/2001 Kates et al.
6,278,786 B1 8/2001 McIntosh
6,282,176 B1 8/2001 Hemkumar
6,304,179 B1 10/2001 Lotito et al.
6,317,501 B1 11/2001 Matsuo
6,418,228 B1 7/2002 Terai et al.
6,434,246 B1 8/2002 Kates et al.
6,434,247 B1 8/2002 Kates et al.
6,445,799 B1 9/2002 Taenzer et al.
6,522,746 B1 2/2003 Marchok et al.
6,542,436 B1 4/2003 Myllyla
6,650,701 B1 11/2003 Hsiang et al.
6,683,960 B1 1/2004 Fujii et al.
6,738,482 B1 5/2004 Jaber
6,766,292 B1 7/2004 Chandran
6,768,795 B2 7/2004 Feltstrom et al.
6,792,107 B2 9/2004 Tucker et al.
6,850,617 B1 2/2005 Weigand
6,940,982 B1 9/2005 Watkins
7,016,504 B1 3/2006 Shennib
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,466,838 B1 12/2008 Mosely
7,680,456 B2 3/2010 Muhammad et al.
7,742,746 B2 6/2010 Xiang et al.
7,742,790 B2 6/2010 Konchitsky et al.
7,817,808 B2 10/2010 Konchitsky et al.
7,953,231 B2 5/2011 Ishida
8,019,050 B2 9/2011 Mactavish et al.
8,085,966 B2 12/2011 Amsel
8,165,312 B2 * 4/2012 Clemow ............ G10K 11/1788 381/71.1
D666,169 S 8/2012 Tucker et al.
8,249,262 B2 8/2012 Chua et al.
8,251,903 B2 8/2012 LeBoeuf et al.
8,290,537 B2 10/2012 Lee et al.
8,325,934 B2 12/2012 Kuo
8,331,604 B2 12/2012 Saito et al.
8,374,358 B2 2/2013 Buck et al.
8,379,884 B2 2/2013 Horibe et al.
8,401,200 B2 3/2013 Tiscareno et al.
8,442,251 B2 5/2013 Jensen et al.
8,559,661 B2 10/2013 Tanghe
8,600,085 B2 12/2013 Chen et al.
8,775,172 B2 7/2014 Konchitsky et al.
8,804,974 B1 8/2014 Melanson
8,831,239 B2 9/2014 Bakalos
8,842,848 B2 9/2014 Donaldson et al.
8,855,330 B2 10/2014 Taenzer
8,908,877 B2 12/2014 Abdollahzadeh Milani et al.
8,942,976 B2 1/2015 Li et al.
8,977,545 B2 3/2015 Zeng et al.
9,066,176 B2 6/2015 Hendrix et al.
9,071,724 B2 6/2015 Do et al.
9,082,391 B2 7/2015 Yermeche et al.
9,129,586 B2 9/2015 Bajic et al.
2001/0053228 A1 12/2001 Jones
2002/0003887 A1 1/2002 Zhang et al.
2003/0063759 A1 4/2003 Brennan et al.
2003/0072439 A1 4/2003 Gupta
2003/0185403 A1 10/2003 Sibbald
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0018460 A1 1/2006 McCree
2006/0035593 A1 2/2006 Leeds
2006/0055910 A1 3/2006 Lee
2006/0069556 A1 3/2006 Nadjar et al.
2006/0153400 A1 7/2006 Fujita et al.
2006/0159282 A1 7/2006 Borsch
2006/0161428 A1 7/2006 Fouret
2006/0251266 A1 11/2006 Saunders et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0177532 A1 7/2008 Greiss et al.
2008/0181422 A1 7/2008 Christoph
2008/0226098 A1 9/2008 Haulick et al.
2008/0240413 A1 10/2008 Mohammed et al.
2008/0240455 A1 10/2008 Inoue et al.
2008/0240457 A1 10/2008 Inoue et al.
2008/0269926 A1 10/2008 Xiang et al.
2009/0012783 A1 1/2009 Klein
2009/0034748 A1 2/2009 Sibbald
2009/0041260 A1 2/2009 Jorgensen et al.
2009/0046867 A1 2/2009 Clemow
2009/0060222 A1 3/2009 Jeong et al.
2009/0080670 A1 3/2009 Solbeck et al.
2009/0086990 A1 4/2009 Christoph
2009/0175461 A1 7/2009 Nakamura et al.
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima

(56) References Cited

U.S. PATENT DOCUMENTS

2009/0304200 A1 12/2009 Kim et al.
2009/0311979 A1 12/2009 Husted et al.
2010/0002891 A1 1/2010 Shiraishi et al.
2010/0014683 A1 1/2010 Maeda et al.
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0098265 A1 4/2010 Pan et al.
2010/0124335 A1 5/2010 Wessling et al.
2010/0124336 A1 5/2010 Shridhar et al.
2010/0124337 A1 5/2010 Wertz et al.
2010/0131269 A1 5/2010 Park et al.
2010/0142715 A1 6/2010 Goldstein et al.
2010/0150367 A1 6/2010 Mizuno
2010/0158330 A1 6/2010 Guissin et al.
2010/0166203 A1 7/2010 Peissig et al.
2010/0195838 A1 8/2010 Bright
2010/0195844 A1 8/2010 Christoph et al.
2010/0207317 A1 8/2010 Iwami et al.
2010/0239126 A1 9/2010 Grafenberg et al.
2010/0246855 A1 9/2010 Chen
2010/0260345 A1 10/2010 Shridhar et al.
2010/0266137 A1 10/2010 Sibbald et al.
2010/0272276 A1 10/2010 Carreras et al.
2010/0272283 A1 10/2010 Carreras et al.
2010/0274564 A1 10/2010 Bakalos et al.
2010/0284546 A1 11/2010 DeBrunner et al.
2010/0291891 A1 11/2010 Ridgers et al.
2010/0296666 A1 11/2010 Lin
2010/0296668 A1 11/2010 Lee et al.
2010/0310086 A1 12/2010 Magrath et al.
2010/0322430 A1 12/2010 Isberg
2011/0007907 A1 1/2011 Park et al.
2011/0026724 A1 2/2011 Doclo
2011/0099010 A1 4/2011 Zhang
2011/0106533 A1 5/2011 Yu
2011/0116654 A1 5/2011 Chan et al.
2011/0129098 A1 6/2011 Delano et al.
2011/0130176 A1 6/2011 Magrath et al.
2011/0142247 A1 6/2011 Fellers et al.
2011/0144984 A1 6/2011 Konchitsky
2011/0158419 A1 6/2011 Theverapperuma et al.
2011/0206214 A1 8/2011 Christoph et al.
2011/0222698 A1 9/2011 Asao et al.
2011/0249826 A1 10/2011 Van Leest
2011/0288860 A1 11/2011 Schevciw et al.
2011/0293103 A1 12/2011 Park et al.
2011/0299695 A1 12/2011 Nicholson
2011/0305347 A1 12/2011 Wurm
2011/0317848 A1 12/2011 Ivanov et al.
2012/0135787 A1 5/2012 Kusunoki et al.
2012/0140917 A1 6/2012 Nicholson et al.
2012/0140942 A1 6/2012 Loeda
2012/0140943 A1 6/2012 Hendrix et al.
2012/0148062 A1 6/2012 Scarlett et al.
2012/0155666 A1* 6/2012 Nair .................... G10K 11/178 381/71.6
2012/0170766 A1 7/2012 Alves et al.
2012/0207317 A1 8/2012 Abdollahzadeh Milani et al.
2012/0215519 A1 8/2012 Park et al.
2012/0250873 A1 10/2012 Bakalos et al.
2012/0259626 A1 10/2012 Li et al.
2012/0263317 A1 10/2012 Shin et al.
2012/0281850 A1 11/2012 Hyatt
2012/0300955 A1 11/2012 Iseki et al.
2012/0300958 A1 11/2012 Klemmensen
2012/0300960 A1 11/2012 Mackay et al.
2012/0308021 A1 12/2012 Kwatra et al.
2012/0308024 A1 12/2012 Alderson et al.
2012/0308025 A1 12/2012 Hendrix et al.
2012/0308026 A1 12/2012 Kamath et al.
2012/0308027 A1 12/2012 Kwatra
2012/0308028 A1 12/2012 Kwatra et al.
2012/0310640 A1 12/2012 Kwatra et al.
2013/0010982 A1 1/2013 Elko et al.
2013/0083939 A1 4/2013 Fellers et al.
2013/0195282 A1 8/2013 Ohita et al.
2013/0243198 A1 9/2013 Van Rumpt
2013/0243225 A1 9/2013 Yokota
2013/0272539 A1 10/2013 Kim et al.
2013/0287218 A1 10/2013 Alderson et al.
2013/0287219 A1 10/2013 Hendrix et al.
2013/0301842 A1 11/2013 Hendrix et al.
2013/0301846 A1 11/2013 Alderson et al.
2013/0301847 A1 11/2013 Alderson et al.
2013/0301848 A1 11/2013 Zhou et al.
2013/0301849 A1 11/2013 Alderson et al.
2013/0315403 A1 11/2013 Samuelsson
2013/0343556 A1 12/2013 Bright
2013/0343571 A1 12/2013 Rayala et al.
2014/0016803 A1 1/2014 Puskarich
2014/0036127 A1 2/2014 Pong et al.
2014/0044275 A1 2/2014 Goldstein et al.
2014/0050332 A1 2/2014 Nielsen et al.
2014/0072134 A1 3/2014 Po et al.
2014/0086425 A1 3/2014 Jensen et al.
2014/0146976 A1 5/2014 Rundle
2014/0169579 A1 6/2014 Azmi
2014/0177851 A1 6/2014 Kitazawa et al.
2014/0211953 A1 7/2014 Alderson et al.
2014/0270222 A1 9/2014 Hendrix et al.
2014/0270223 A1 9/2014 Li et al.
2014/0270224 A1 9/2014 Zhou et al.
2014/0294182 A1 10/2014 Axelsson et al.
2014/0307887 A1 10/2014 Alderson
2014/0307888 A1 10/2014 Alderson et al.
2014/0307890 A1 10/2014 Zhou et al.
2014/0314244 A1 10/2014 Yong
2014/0314247 A1 10/2014 Zhang
2014/0369517 A1 12/2014 Zhou et al.
2015/0092953 A1 4/2015 Abdollahzadeh Milani et al.
2015/0161981 A1 6/2015 Kwatra

FOREIGN PATENT DOCUMENTS

EP 1691577 A2 8/2006
EP 1880699 A2 1/2008
EP 1947642 A1 7/2008
EP 2133866 A1 12/2009
EP 2216774 A1 8/2010
EP 2237573 A1 10/2010
EP 2395500 A1 12/2011
EP 2395501 A1 12/2011
EP 2551845 A1 1/2013
GB 2401744 A 11/2004
GB 2436657 A 10/2007
GB 2455821 A 6/2009
GB 2455824 A 6/2009
GB 2455828 A 6/2009
GB 2484722 A 4/2012
JP H06-186985 A 7/1994
JP 07104769 4/1995
JP 07240989 9/1995
JP 07325588 12/1995
JP H11305783 A 11/1999
JP 2008015046 A 1/2008
WO WO 9113429 9/1991
WO WO 9911045 3/1999
WO WO 03/015074 A1 2/2003
WO WO 03015275 A1 2/2003
WO WO 2004009007 A1 1/2004
WO WO 2004017303 A1 2/2004
WO WO 2006128768 A1 12/2006
WO WO 2007007916 A1 1/2007
WO WO 2007011337 1/2007
WO WO 2007110807 A2 10/2007
WO WO 2007113487 A1 11/2007
WO WO 2010117714 A1 10/2010

(56) References Cited

FOREIGN PATENT DOCUMENTS

WO WO 2010131154 A1 11/2010
WO WO 2012134874 A1 10/2012
WO WO 2015038255 A1 3/2015

OTHER PUBLICATIONS

U.S. Appl. No. 13/795,160, filed Mar. 12, 2013, Hendrix, et al.
U.S. Appl. No. 13/692,367, filed Dec. 3, 2012, Alderson, et al.
U.S. Appl. No. 13/722,119, filed Dec. 20, 2012, Hendrix, et al.
U.S. Appl. No. 13/727,718, filed Dec. 27, 2012, Alderson, et al.
U.S. Appl. No. 13/784,018, filed Mar. 4, 2013, Alderson, et al.
U.S. Appl. No. 13/787,906, filed Mar. 7, 2013, Alderson, et al.
U.S. Appl. No. 13/729,141, filed Dec. 28, 2012, Zhou, et al.
U.S. Appl. No. 13/794,931, filed Mar. 12, 2013, Lu, et al.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
Campbell, Mikey, "Apple looking into self-adjusting earbud headphones with noise cancellation tech", Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. "A simultaneous equation method-based online secondary path modeling algorithm for active noise control", Journal of Sound and Vibration, Apr. 25, 2007, pp. 455-474, vol. 303, No. 3-5, London, GB.
Erkelens, et al., "Tracking of Nonstationary Noise Based on Data-Driven Recursive Noise Power Estimation", IEEE Transactions on Audio Speech and Language Processing, Aug. 2008, pp. 1112-1123, vol. 16, No. 6, Piscataway, NJ, US.
Rao, et al., "A Novel Two State Single Channel Speech Enhancement Technique", India Conference (INDICON) 2011 Annual IEEE, IEEE, Dec. 2011, 6 pages (pp. 1-6 in pdf), Piscataway, NJ, US.
Rangachari, et al., "A noise-estimation algorithm for highly non-stationary environments", Speech Communication, Feb. 2006, pp. 220-231, vol. 48, No. 2. Elsevier Science Publishers.
Parkins, et al., "Narrowband and broadband active control in an enclosure using the acoustic energy density", J. Acoust. Soc. Am. Jul. 2000, pp. 192-203, vol. 108, issue 1, US.
Feng, et al.., "A broadband self-tuning active noise equaliser", Signal Processing, Oct. 1, 1997, pp. 251-256, vol. 62, No. 2, Elsevier Science Publishers B.V. Amsterdam, NL.
Zhang, et al., "A Robust Online Secondary Path Modeling Method with Auxiliary Noise Power Scheduling Strategy and Norm Constraint Manipulation", IEEE Transactions on Speech and Audio Processing, IEEE Service Center, Jan. 1, 2003, pp. 45-53, vol. 11, No. 1, NY.
Lopez-Gaudana, et al., "A hybrid active noise cancelling with secondary path modeling", 51st Midwest Symposium on Circuits and Systems, MWSCAS 2008, Aug. 10-13, 2008, pp. 277-280, IEEE, Knoxville, TN.
U.S. Appl. No. 14/029,159, filed Sep. 17, 2013, Li, et al.
U.S. Appl. No. 14/062,951, filed Oct. 25, 2013, Zhou, et al.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 14/252,235, filed Apr. 14, 2014, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and the Hybrid Solution", Adaptive Filtering Applications, Dr. Lino Garcia (Ed.), Jul. 2011, pp. 49-84, ISBN: 978-953-307-306-4, InTech.

(56) References Cited

OTHER PUBLICATIONS

Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.
Hurst, et al., "An improved double sampling scheme for switched-capacitor delta-sigma modulators", 1992 IEEE Int. Symp. on Circuits and Systems, May 10-13, 1992, vol. 3, pp. 1179-1182, San Diego, CA.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
U.S. Appl. No. 14/197,814, filed Mar. 5, 2014, Kaller, et al.
U.S.Appl. No. 14/210,537, filed Mar. 14, 2014, Abdollahzadeh Milani, et al.
U.S. Appl. No. 14/210,589, filed Mar. 14, 2014, Abdollahzadeh Milani, et al.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS One, Nov. 2012, pp. 1-7, vol. 7, Issue 11, e49370, Ontario, Canada.
U.S. Appl. No. 13/968,007, filed Aug. 15, 2013, Hendrix, et al.
U.S. Appl. No. 14/656,124, filed Mar. 12, 2015, Hendrix, et al.
U.S. Appl. No. 14/578,567, filed Dec. 22, 2014, Kwatra, et al.
Widrow, B., et al., Adaptive Noise Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
U.S. Appl. No. 14/734,321, filed Jun. 9, 2015, Alderson, et al.
U.S. Appl. No. 14/840,831, filed Aug. 31, 2015, Hendrix, et al.
Rafaely, Boaz, "Active Noise Reducing Headset—an Overview", The 2001 International Congress and Exhibition on Noice Control Engineering, Aug. 27-30, 2001, 10 pages (pp. 1-10 in pdf), The Netherlands.
Ray, et al., "Hybrid Feedforward-Feedback Active Noise Reduction for Hearing Protection and Communication", The Journal of the Acoustical Society of America. American Institute of Physics for the Acoustical Society of American, Jan. 2006, pp. 2026-2036, vol. 120, No. 4, New York, NY.

* cited by examiner

INTERNAL DYNAMIC RANGE CONTROL IN AN ADAPTIVE NOISE CANCELLATION (ANC) SYSTEM

BACKGROUND OF THE INVENTION

1. Field of the Invention

The present invention relates generally to personal audio devices such as headphones that include adaptive noise cancellation (ANC), and, more specifically, to architectural features of an ANC system in which dynamic range of signal pathways is improved by filtering images.

2. Background of the Invention

Wireless telephones, such as mobile/cellular telephones, cordless telephones, and other consumer audio devices, such as MP3 players, are in widespread use. Performance of such devices with respect to intelligibility can be improved by providing adaptive noise canceling (ANC) using a reference microphone to measure ambient acoustic events and then using signal processing to insert an anti-noise signal having an adaptive characteristic into the output of the device to cancel the ambient acoustic events.

The dynamic range of digital audio signal processors, such as the ANC system described above, is set by the width of the signal pathways, which provides a trade-off in circuit complexity, power consumption, and area. Under certain ambient conditions, the dynamic range requirement of an ANC system may be much greater than under nominal conditions, but in order to avoid clipping distortion, the dynamic range of the signal pathways must be sufficient to support the range of signals encountered during operation.

Therefore, it would be desirable to provide a personal audio device, including a wireless telephone that provides noise cancellation that has dynamic range sufficient to avoid clipping distortion, while maintaining low power operation and without requiring significantly larger circuit area.

SUMMARY OF THE INVENTION

The above-stated objectives of providing a personal audio device having adaptive noise cancellation (ANC) without clipping distortion while maintaining low power operation and without requiring significantly larger circuit area, is accomplished in a personal audio system, a method of operation, and an integrated circuit.

The personal audio device includes an output transducer for reproducing an audio signal that includes both source audio for playback to a listener, and an anti-noise signal for countering the effects of ambient audio sounds in an acoustic output of the transducer. The personal audio device also includes the integrated circuit to provide adaptive noise-canceling (ANC) functionality. The method is a method of operation of the personal audio system and integrated circuit. One or more microphones are mounted on the device housing to provide a signal indicative of the ambient audio sounds and optionally the output of the transducer. The personal audio system further includes an ANC processing circuit for adaptively generating an anti-noise signal from the one or more microphone signals, such that the anti-noise signal causes substantial cancellation of the ambient audio sounds. One or more adaptive filters are used to generate the anti-noise signal from the one or more microphone signals, which are quantized by a delta-sigma analog-to-digital converter (ADC), a separate delta-sigma noise shaper, or both. The ANC processing circuit further implements a low-pass filter that removes quantization noise images at the output of the adaptive filter to reduce the dynamic required at the output of the adaptive filter.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses noise-canceling techniques and circuits that can be implemented in a personal audio system, such as a wireless telephone and connected earbuds. The personal audio system includes an adaptive noise canceling (ANC) circuit that measures the ambient acoustic environment at the earbuds or other output transducer and generates a signal that is injected in the speaker (or other transducer) output to cancel ambient acoustic events. One or more microphones are provided to measure the ambient acoustic environment, which is used to generate an anti-noise signal provided to the speaker to cancel the ambient audio sounds. One or more adaptive filters are used to generate the anti-noise signal from the one or more microphone signals, which are quantized by a delta-sigma analog-to-digital converter (ADC), a separate delta-sigma noise shaper, or both. The ANC processing circuit further implements a low-pass filter that removes quantization noise images at the output of the adaptive filter to reduce the dynamic required at the output of the adaptive filter. Since ANC performance is strongly affected by the latency of the anti-noise signal path, inserting filters in series with the adaptive filter will reduce performance due to increased latency. Therefore, there is a tradeoff between the dynamic range required to represent the output of the adaptive filter without clipping, and the latency of an ANC system that includes filtering of the adaptive filter output. The corner frequency of the low-pass filter is chosen to provide the best compromise between the dynamic range margin available for the anti-noise signal, and/or other internal signal paths that have quantization noise images, and the latency of the ANC system.

Figure 1A:
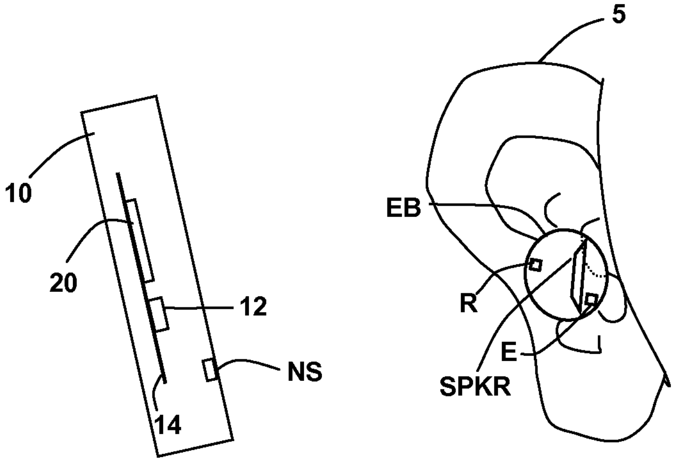
FIG. 1A is an illustration of a wireless telephone 10 coupled to an earbud EB, which is an example of a personal audio device in which the techniques disclosed herein can be implemented.

FIG. 1A shows a wireless telephone 10 proximate to a human ear 5. Illustrated wireless telephone 10 is an example of a device in which the techniques herein may be employed, but it is understood that not all of the elements or configurations illustrated in wireless telephone 10, or in the circuits depicted in subsequent illustrations, are required. Wireless telephone 10 is connected to an earbud EB by a wired or wireless connection, e.g., a BLUETOOTH™ connection (BLUETOOTH is a trademark or Bluetooth SIG, Inc.). Earbud EB has a transducer, such as a speaker SPKR, which reproduces source audio including distant speech received from wireless telephone 10, ringtones, stored audio program material, and injection of near-end speech (i.e., the speech of the user of wireless telephone 10). The source audio also includes any other audio that wireless telephone 10 is required to reproduce, such as source audio from web-pages or other network communications received by wireless telephone 10 and audio indications such as battery low and other system event notifications. A reference microphone R is provided on a surface of a housing of earbud EB for measuring the ambient acoustic environment. Another microphone, error microphone E, is provided in order to further improve the ANC operation by providing a measure of the ambient audio combined with the audio reproduced by speaker SPKR close to ear 5, when earbud EB is inserted in the outer portion of ear 5. While the illustrated example shows an earspeaker implementation of a noise-canceling system, the techniques disclosed herein can also be implemented in a wireless telephone or other personal audio device, in which the output transducer and reference/error microphones are all provided on a housing of the wireless telephone or other personal audio device.

Wireless telephone 10 includes adaptive noise canceling (ANC) circuits and features that inject an anti-noise signal into speaker SPKR to improve intelligibility of the distant speech and other audio reproduced by speaker SPKR. An exemplary circuit 14 within wireless telephone 10 includes an audio CODEC integrated circuit 20 that receives the signals from reference microphone R, near speech microphone NS, and error microphone E and interfaces with other integrated circuits such as an RF integrated circuit 12 containing the wireless telephone transceiver. In other embodiments of the invention, the circuits and techniques disclosed herein may be incorporated in a single integrated circuit that contains control circuits and other functionality for implementing the entirety of the personal audio device, such as an MP3 player-on-a-chip integrated circuit. Alternatively, the ANC circuits may be included within a housing of earbud EB or in a module located along a wired connection between wireless telephone 10 and earbud EB. For the purposes of illustration, the ANC circuits will be described as provided within wireless telephone 10, but the above variations are understandable by a person of ordinary skill in the art and the consequent signals that are required between earbud EB, wireless telephone 10 and a third module, if required, can be easily determined for those variations. A near speech microphone NS is provided at a housing of wireless telephone 10 to capture near-end speech, which is transmitted from wireless telephone 10 to the other conversation participant(s). Alternatively, near speech microphone NS may be provided on the outer surface of a housing of earbud EB, or on a boom (microphone extension) affixed to earbud EB.

Figure 1B:
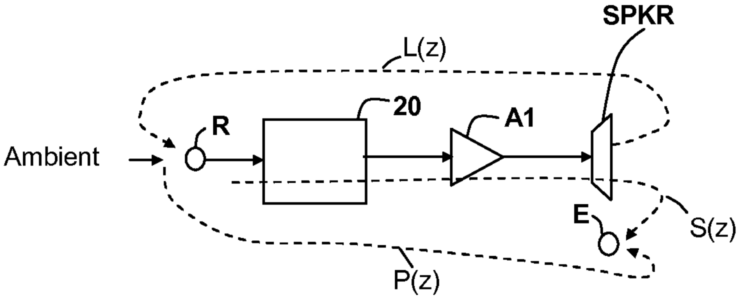
FIG. 1B is an illustration of electrical and acoustical signal paths in FIG. 1A.

FIG. 1B shows a simplified schematic diagram of audio CODEC integrated circuit 20 that includes ANC processing, as coupled to reference microphone R, which provides a measurement of ambient audio sounds Ambient that is filtered by the ANC processing circuits within audio CODEC integrated circuit 20. Audio CODEC integrated circuit 20 generates an output that is amplified by an amplifier A1 and is provided to speaker SPKR. Audio CODEC integrated circuit 20 receives the signals (wired or wireless depending on the particular configuration) from reference microphone R, near speech microphone NS and error microphone E and interfaces with other integrated circuits such as RF integrated circuit 12 containing the wireless telephone transceiver. In other configurations, the circuits and techniques disclosed herein may be incorporated in a single integrated circuit that contains control circuits and other functionality for implementing the entirety of the personal audio device, such as an MP3 player-on-a-chip integrated circuit. Alternatively, multiple integrated circuits may be used, for example, when a wireless connection is provided from earbud EB to wireless telephone 10 and/or when some or all of the ANC processing is performed within earbud EB or a module disposed along a cable connecting wireless telephone 10 to earbud EB.

In general, the ANC techniques illustrated herein measure ambient acoustic events (as opposed to the output of speaker SPKR and/or the near-end speech) impinging on reference microphone R, and also measure the same ambient acoustic events impinging on error microphone E. The ANC processing circuits of illustrated wireless telephone 10 adapt an anti-noise signal generated from the output of reference microphone R to have a characteristic that minimizes the amplitude of the ambient acoustic events at error microphone E. Since acoustic path P(z) extends from reference microphone R to error microphone E, the ANC circuits are essentially estimating acoustic path P(z) combined with removing effects of an electro-acoustic path S(z) that represents the response of the audio output circuits of CODEC IC 20 and the acoustic/electric transfer function of speaker SPKR. The estimated response includes the coupling between speaker SPKR and error microphone E in the particular acoustic environment which is affected by the proximity and structure of ear 5 and other physical objects and human head structures that may be in proximity to earbud EB. Leakage, i.e., acoustic coupling, between speaker SPKR and reference microphone R can cause error in the anti-noise signal generated by the ANC circuits within CODEC IC 20. In particular, desired downlink speech and other internal audio intended for reproduction by speaker SPKR can be partially canceled due to the leakage path L(z) between speaker SPKR and reference microphone R. Since audio measured by reference microphone R is considered to be ambient audio that generally should be canceled, leakage path L(z) represents the portion of the downlink speech and other internal audio that is present in the reference microphone signal and causes the above-described erroneous operation. Therefore, the ANC circuits within CODEC IC 20 include leakage-path modeling circuits that compensate for the presence of leakage path L(z). While the illustrated wireless telephone 10 includes a two microphone ANC system with a third near speech microphone NS, a system may be constructed that does not include separate error and reference microphones. Alternatively, when near speech microphone NS is located proximate to speaker SPKR and error microphone E, near speech microphone NS may be used to perform the function of the reference microphone R. Also, in personal audio devices designed only for audio playback, near speech microphone NS will generally not be included, and the near speech signal paths in the circuits described in further detail below can be omitted.

Figure 2:
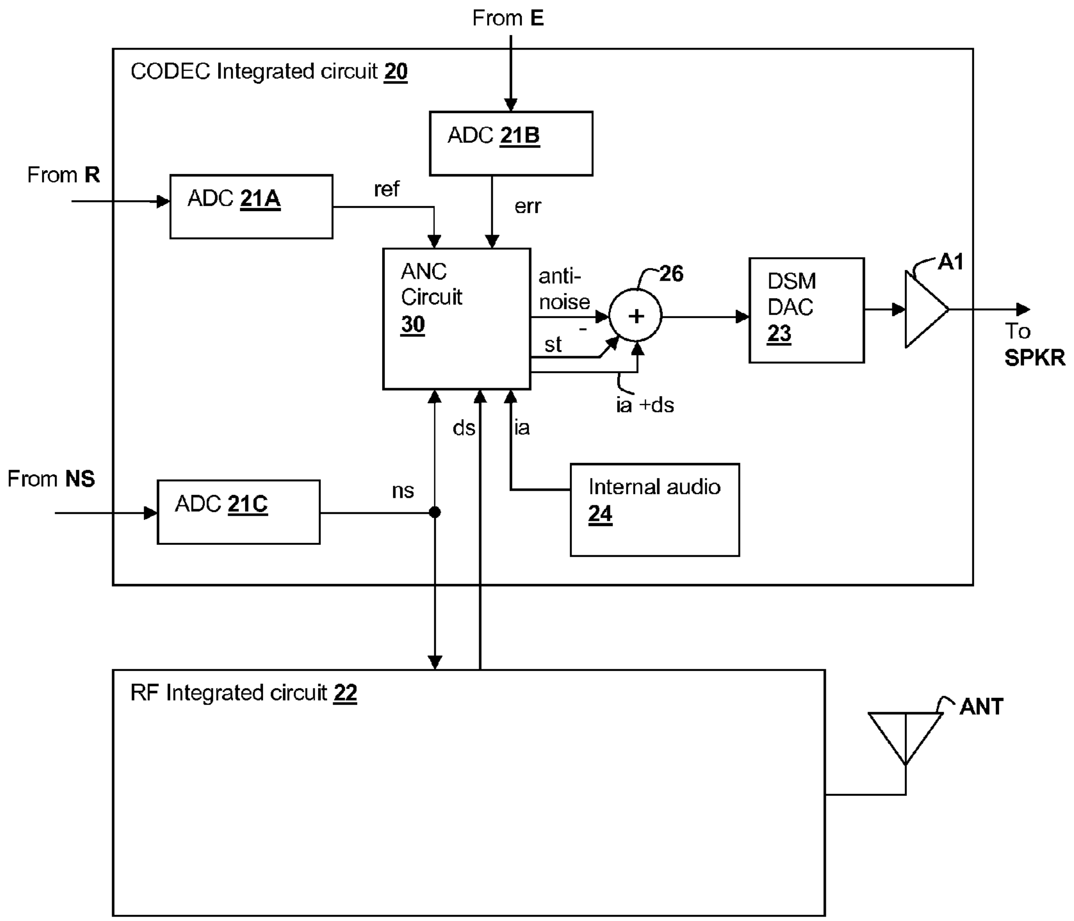
FIG. 2 is a block diagram of circuits within wireless telephone 10 and/or earbud EB of FIG. 1A.

Referring now to FIG. 2, circuits within wireless telephone 10 are shown in a block diagram. The circuit shown in FIG. 2 further applies to the other configurations mentioned above, except that signaling between CODEC integrated circuit 20 and other units within wireless telephone 10 are provided by cables or wireless connections when CODEC integrated circuit 20 is located outside of wireless telephone 10. In such a configuration, signaling between CODEC integrated circuit 20 and error microphone E, reference microphone R and speaker SPKR are provided by wired or wireless connections when CODEC integrated circuit 20 is located within wireless telephone 10. CODEC integrated circuit 20 includes an analog-to-digital converter (ADC) 21A for receiving the reference microphone signal and generating a digital representation ref of the reference microphone signal. CODEC integrated circuit 20 also includes an ADC 21B for receiving the error microphone signal and generating a digital representation err of the error microphone signal, and an ADC 21C for receiving the near speech microphone signal and generating a digital representation ns of the error microphone signal. CODEC IC 20 generates an output for driving speaker SPKR from amplifier A1, which amplifies the output of a delta-sigma modulated digital-to-analog converter (DAC) 23 that receives the output of a combiner 26. Combiner 26 combines audio signals is from internal audio sources 24, and the anti-noise signal anti-noise generated by an ANC circuit 30, which by convention has the same polarity as the noise in reference microphone signal ref and is therefore subtracted by combiner 26. Combiner 26 also combines an attenuated portion of near speech signal ns, i.e., sidetone information st, so that the user of wireless telephone 10 hears their own voice in proper relation to downlink speech ds, which is received from a radio frequency (RF) integrated circuit 22. Near speech signal ns is also provided to RF integrated circuit 22 and is transmitted as uplink speech to the service provider via antenna ANT.

Figure 3A:
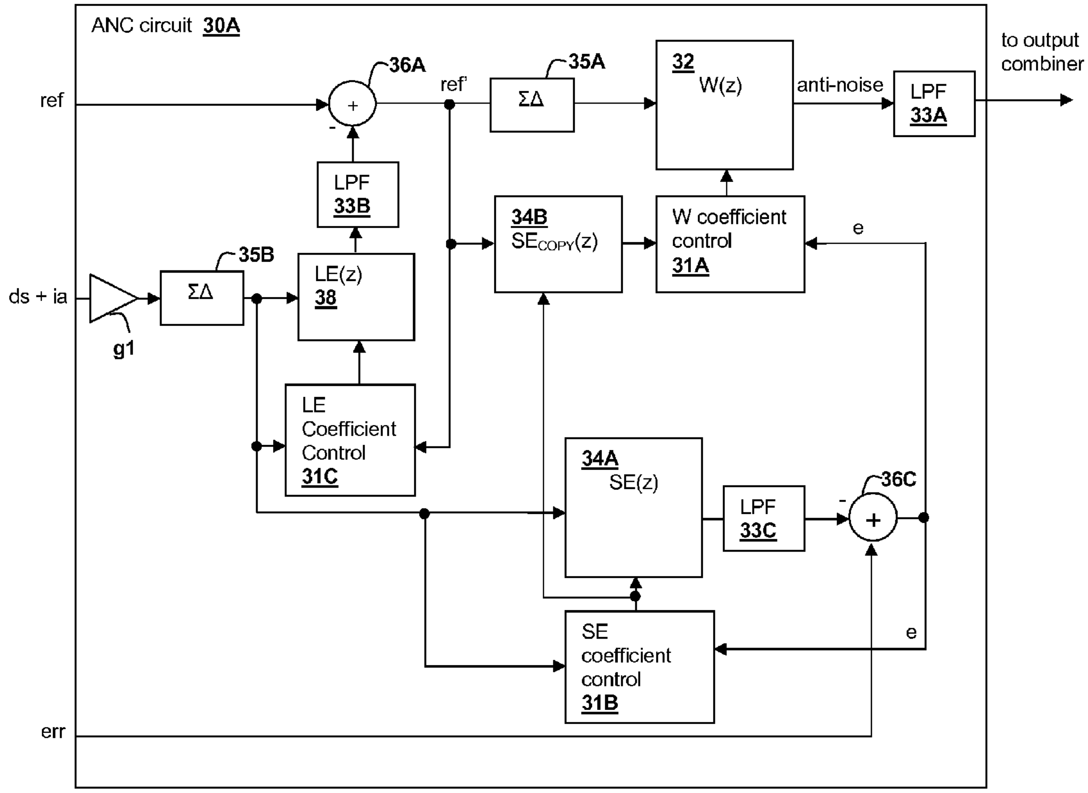
FIG. 3A is a block diagram depicting one example of an ANC circuit 30A that can be used to implement ANC circuit 30 of CODEC integrated circuit 20 of FIG. 2.

Referring now to FIG. 3A, details of ANC circuit 30A are shown that can be used to implement ANC circuit 30 of FIG. 2. A combiner 36A removes an estimated leakage signal from reference microphone signal ref, which in the example is provided by a leakage-path adaptive filter 38 having a response LE(z) that models leakage path L(z). Combiner 36A generates a leakage-corrected reference microphone signal ref'. A delta-sigma shaper 35A is used to quantize leakage-corrected reference microphone signal ref', which reduces the width of subsequent processing stages. Details of a system architecture in which delta-sigma shapers are employed to decrease the width of filters are disclosed in U.S. Patent Application Publication U.S. 20120308025A1 entitled "AN ADAPTIVE NOISE CANCELING ARCHITECTURE FOR A PERSONAL AUDIO DEVICE", the disclosure of which is incorporated herein by reference. An adaptive filter 32 receives delta-sigma modulated leakage-corrected reference microphone signal ref' and under ideal circumstances, adapts its transfer function W(z) to be P(z)/S(z) to generate anti-noise signal anti-noise, which is provided to an output combiner that combines the anti-noise signal with the audio to be reproduced by speaker SPKR, as exemplified by combiner 26 of FIG. 2. The coefficients of adaptive filter 32 are controlled by a W coefficient control block 31A that uses a correlation of two signals to determine the response of adaptive filter 32, which generally minimizes the error, in a least-mean squares sense, between those components of leakage-corrected reference microphone signal ref' present in error microphone signal err. The signals processed by W coefficient control block 31A are the leakage-corrected reference microphone signal ref' shaped by a copy of an estimate of the response of path S(z) (i.e., response $SE_{COPY}(z)$) provided by filter 34B and another signal that includes error microphone signal err. By transforming leakage-corrected reference microphone signal ref' with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z).

Figure 5:
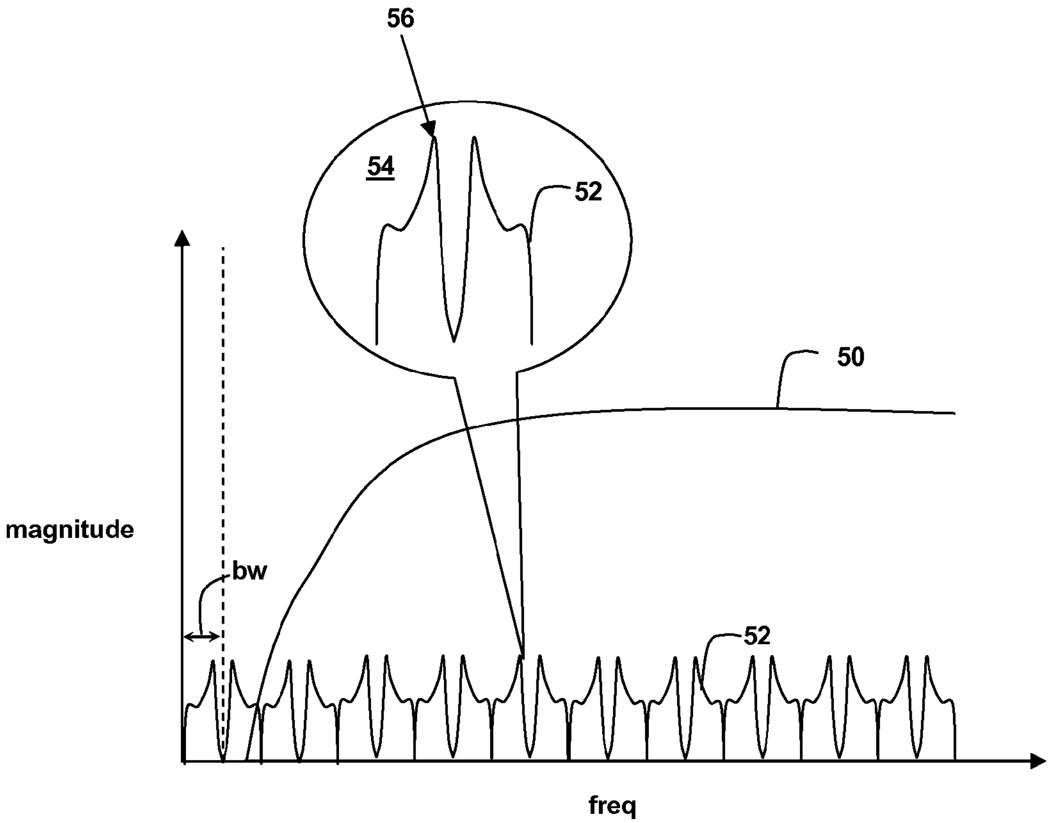
FIG. 5 is a waveform diagram depicting signals within the circuits depicted in FIG. 2 and FIGS. 3A-3B.
Figure 6:
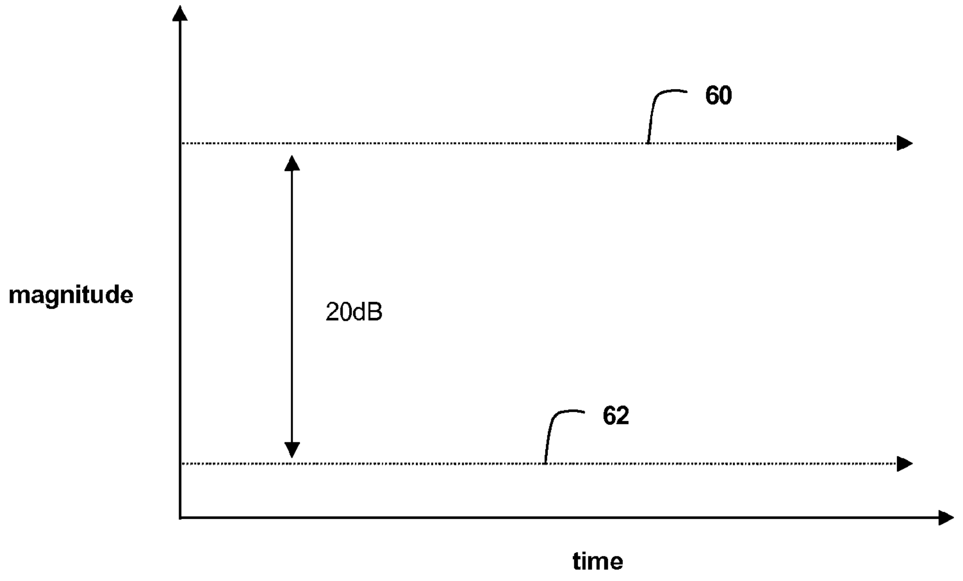
FIG. 6 is another waveform diagram depicting signals within the circuits depicted in FIG. 2 and FIGS. 3A-3B.

The output of adaptive filter 32 is processed by a digital low-pass filter 33A that removes signal energy that exists above the operational band of adaptive filter 32, i.e., above the audio frequency range to which W coefficient control block 31A adapts the response of adaptive filter 32. Since response W(z) may have a high gain at some frequencies, at higher audio frequencies when response S(z) has low amplitude as when wireless telephone 10 is off-ear, the amplitude of anti-noise signal anti-noise is increased. Anti-noise signal anti-noise contains not only audio components, but the quantization noise introduced by delta-sigma shaper 35A as multiplied by images of response W(z) repeated at frequency intervals corresponding to the sample rate of adaptive filter 32 divided by the oversampling ratio of the signal at the input to the adaptive filter 32. Thus, an increase in the gain of adaptive filter 32 not only increases the amplitude of in-band components of anti-noise signal anti-noise, but out-of-band quantization noise, as well. Referring to FIG. 5, an illustration of the frequency distribution of quantization noise 50 is shown with respect to a wideband response 52 of adaptive filter 32. A detail 54 of wideband response 52 of adaptive filter 32 is shown to illustrate a condition in which a high amplitude peak 56 is present in response W(z) due to wireless telephone 10 being off-ear. Such a condition is an example of a condition in which wideband response 52 of adaptive filter 32 might cause clipping due to the product of wideband response 52 and quantization noise 50 which will have significant energy above an audio band of interest bw. Typically, quantization noise in anti-noise signal anti-noise would not be filtered, since transducer SPKR would not be able to physically reproduce those out-of-band components. However, due to the wide dynamic range that response W(z) may have to assume under different ambient conditions, low-pass filter 33A provides a mechanism to reduce the impact of increases in the magnitude of W(z) on the dynamic range of anti-noise signal anti-noise, which could cause clipping if insufficient digital signal width were unavailable to reproduce the full spectrum of anti-noise signal anti-noise. Referring to FIG. 6, a graph showing a first peak amplitude 60 of anti-noise signal anti-noise without low-pass filter 33A and a second peak amplitude 62 of anti-noise signal anti-noise with low-pass filter 33A illustrates an improvement in dynamic range headroom for anti-noise signal anti-noise of 20 dB.

Referring again to FIG. 3A, in addition to error microphone signal err, the other signal processed along with the output of filter 34B by W coefficient control block 31A includes an inverted amount of the source audio (ds+ia) including downlink audio signal ds and internal audio ia. Source audio (ds+ia) has also been processed by a delta-sigma shaper 35B that is similar to delta-sigma shaper 35A, reduces the required width of the filters that follow in the signal path, including leakage path adaptive filter 38 and a secondary path adaptive filter 34A. Source audio (ds+ia) is processed by secondary path adaptive filter 34A having response SE(z), of which response $SE_{COPY}(z)$ is a copy. Filter 34B is not an adaptive filter, per se, but has an adjustable response that is tuned to match the response of adaptive filter 34A, so that the response of filter 34B tracks the adapting of secondary path adaptive filter 34A. By injecting an inverted amount of source audio (ds+ia) that has been filtered by response SE(z), adaptive filter 32 is prevented from adapting to the relatively large amount of source audio (ds+ia) present in error microphone signal err. By transforming the inverted copy of downlink audio signal ds and internal audio ia with the estimate of the response of path S(z), the source audio (ds+ia) that is removed from error microphone signal err before processing should match the expected version of downlink audio signal ds and internal audio ia reproduced at error microphone signal err. The source audio (ds+ia) matches the amount of source audio (ds+ia) present in error microphone signal err because the electrical and acoustical path of S(z) is the path taken by source audio (ds+ia) to arrive at error microphone E.

To implement the above, secondary path adaptive filter 34A has coefficients controlled by a SE coefficient control block 31B, which processes the source audio (ds+ia) and error microphone signal err after removal, by a combiner 36C, of the above-described filtered downlink audio signal ds and internal audio ia, that has been filtered by adaptive filter 34A to represent the expected source audio delivered to error microphone E. Adaptive filter 34A is thereby adapted to generate an error signal e from downlink audio signal ds and internal audio ia, that when subtracted from error microphone signal err, contains the content of error microphone signal err that is not due to source audio (ds+ia). Similarly, a LE coefficient control block 31C also is adapted to minimize the components of source audio (ds+ia) present in leakage-corrected reference microphone signal ref', by adapting to generate an output that represents the source audio (ds+ia) present in reference microphone signal ref.

As with adaptive filter 32, both secondary path adaptive filter 34A and leakage path adaptive filter 38 have images that can increase the amplitude of quantization noise introduced by a delta-sigma shaper 35B. Therefore, another low-pass filter 33B is introduced between leakage path adaptive filter 38 and combiner 36A and a low-pass filter 33C is introduced between secondary path adaptive filter 34A and a combiner 36C. Each of low-pass filters 33B and 33C will generally have the same type of amplitude response as low-pass filter 33A, e.g., a first-order low-pass response with a corner frequency above the audio band of interest of the ANC system. Alternatively, higher-order filters could be used. Low pass filters 33A, 33B and 33C are in series with, and thus can be merged with, adaptive filter 32, secondary path adaptive filter 34A, and leakage path adaptive filter 32, respectively. W coefficient control block 31A, SE coefficient control block 31B and LE coefficient control block 31C are prevented from causing the responses of adaptive filter 32, secondary path adaptive filter 34A, and leakage path adaptive filter 32, respectively, to adapt to cancel the responses of low pass filters 33A, 33B and 33C, respectively, since W coefficient control block 31A, SE coefficient control block 31B and LE coefficient control block 31C are operating at the baseband sample rate and not the oversampled rate at which adaptive filter 32, secondary path adaptive filter 34A, and leakage path adaptive filter 32 operate. Further the respective feedback signals that control W coefficient control block 31A, SE coefficient control block 31B and LE coefficient control block 31C are filtered and decimated down to the baseband rate. If significant phase shift is present in the audio band of interest due to any of low-pass filters 33A-33C, corresponding phase-shifts may be introduced as needed to compensate. An exemplary response for low-pass filters 33A-33C might be a single pole roll-off with a corner frequency of 5 times the maximum frequency of the audio band of interest, e.g., 100 kHz for an ANC system with a potential maximum cancellation frequency of 20 kHz.

FIG. 3A also illustrates another feature that may be optionally included to decrease the change of clipping by reducing out-of-band energy in anti-noise signal anti-noise. A gain block g1 is optionally included to multiply the amplitude of source audio (ds+ia) by a gain factor, e.g, 20 dB, prior to delta-sigma shaper 35B. By increasing the gain of the signal path in front of secondary path adaptive filter 34A and leakage path adaptive filter 38, after adaptation, the gains of secondary path adaptive filter 34A and leakage path adaptive filter 38 will be decreased by a corresponding amount. By forcing a lower gain for secondary path adaptive filter 34A and leakage path adaptive filter 38, the images of responses SE(z) and LE(z) that would otherwise multiply the high-frequency quantization noise are reduced. An advantage of lowering the gains of secondary path adaptive filter 34A and leakage path adaptive filter 38, rather than only providing a low-pass filter at their outputs, is that no additional latency is introduced. Both the gain reduction and low-pass filtering can be applied in combination, which can provide for a higher corner frequency of the low-pass filters to achieve similar dynamic range performance to a system without gain reduction and having a lower corner frequency, thus providing lower latency. Increasing the gain before delta-sigma shaper 35B could cause clipping if the amplitude of source audio (ds+ia) becomes too great. However, under such conditions, error microphone E and reference microphone R will generally also be in a clipping condition, due to high amplitude output from transducer SPKR. In addition to reducing the potential for clipping at the outputs of secondary path adaptive filter 34A and leakage path adaptive filter 38, including gain block g1 also provides for increased stability and simplifies the design of decimators included in other portions of the signal path as disclosed in the above-incorporated U.S. Patent Application Publication "AN ADAPTIVE NOISE CANCELING ARCHITECTURE FOR A PERSONAL AUDIO DEVICE." Since there are closed loops present in the ANC system, the decimators must be designed to have unity gain or less for out-of-band energy, so that portions of the ANC system do not become unstable, causing in-band non-linear operation.

Figure 3B:
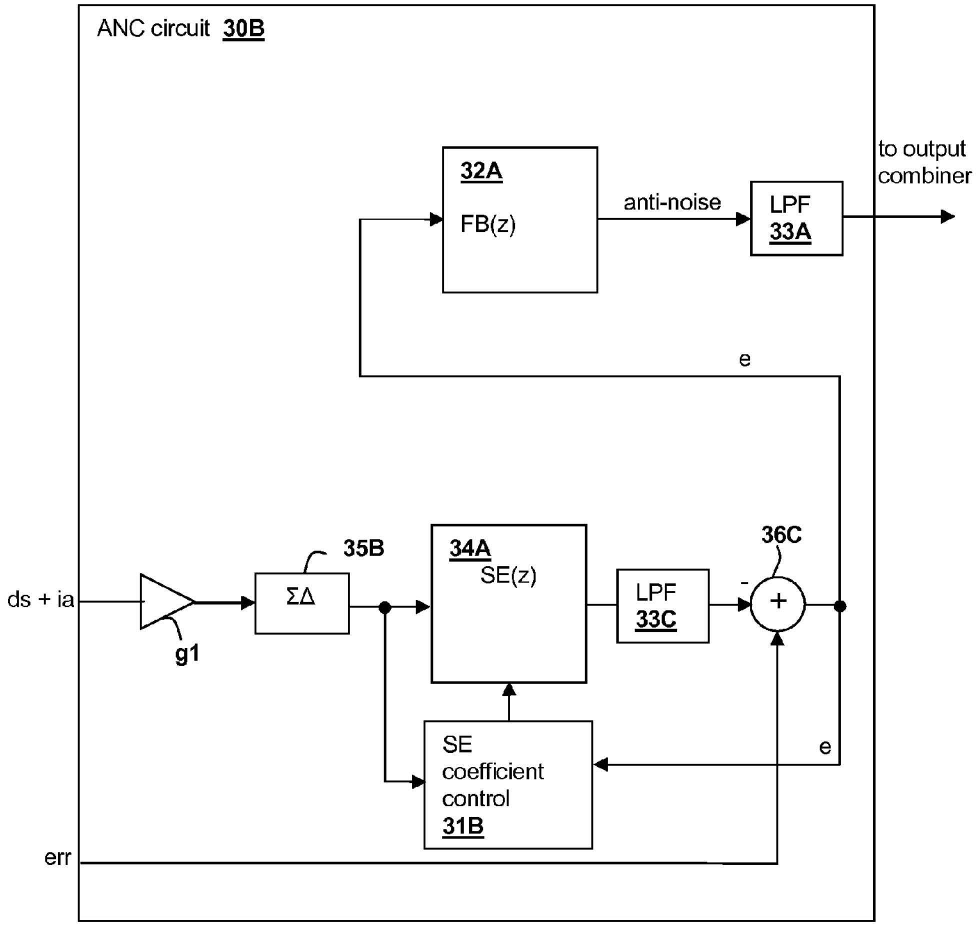
FIG. 3B is a block diagram depicting another example of an ANC circuit 30B that can be used to implement ANC circuit 30 of CODEC integrated circuit 20 of FIG. 2.

FIG. 3B shows another example of details of an alternative ANC circuit 30B that can be used to implement ANC circuit 30 of FIG. 2. ANC circuit 30B is similar to ANC circuit 30A of FIG. 3A, so only differences between ANC circuit 30B and ANC circuit 30A will be discussed below. ANC circuit 30B implements a feedback noise canceling system in which the anti-noise signal is provided by filtering error signal e with a predetermined response FB(z) using a fixed filter 32A. As in ANC circuit 30A of FIG. 3A, low-pass filter 33A filters anti-noise signal anti-noise to remove energy above the audio band of interest that might otherwise cause clipping under certain conditions.

Figure 4:
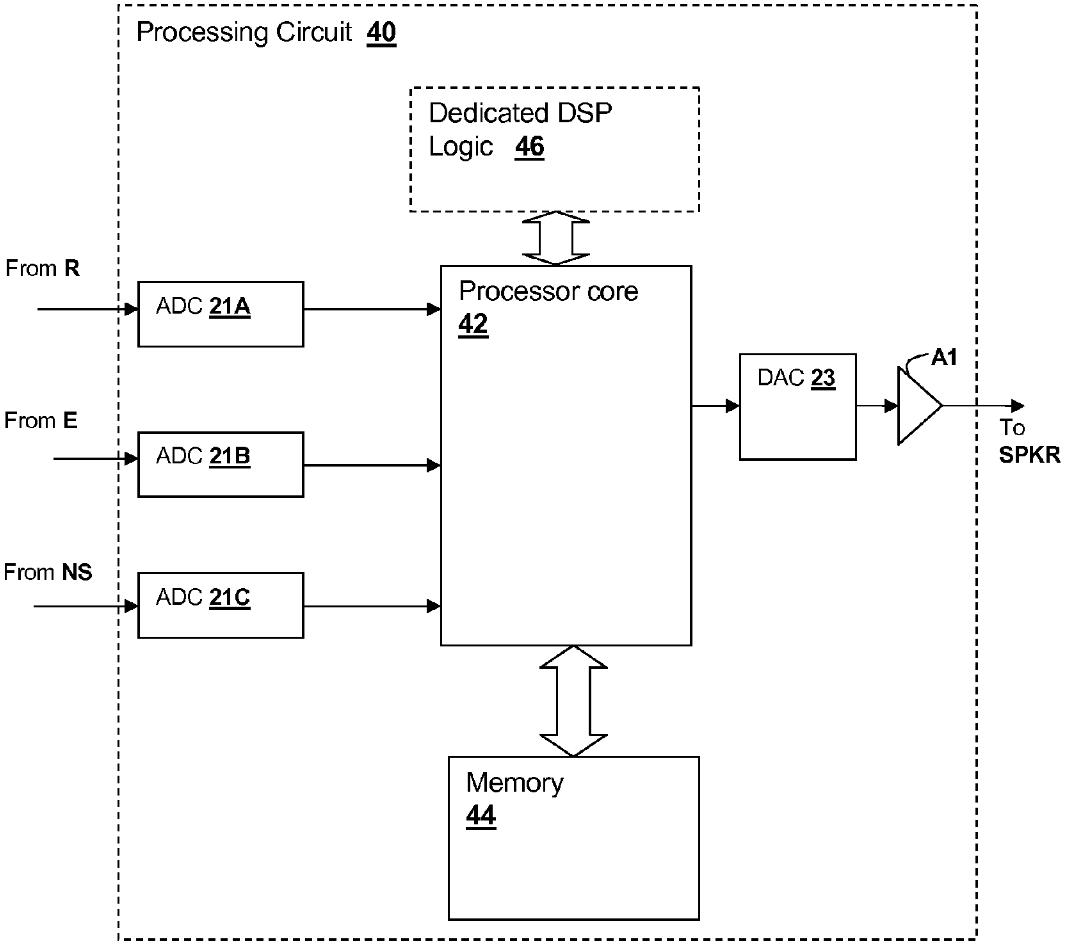
FIG. 4 is a block diagram depicting signal processing circuits and functional blocks that can be used to implement the circuits depicted in FIG. 2 and FIGS. 3A-3B.

Referring now to FIG. 4, a block diagram of an ANC system is shown for implementing ANC techniques as depicted in FIG. 3, and having a processing circuit 40 as may be implemented within CODEC integrated circuit 20 of FIG. 2. Processing circuit 40 includes a processor core 42 coupled to a memory 44 in which are stored program instructions comprising a computer-program product that may implement some or all of the above-described ANC techniques, as well as other signal processing. Optionally, a dedicated digital signal processing (DSP) logic 46 may be provided to implement a portion of, or alternatively all of, the ANC signal processing provided by processing circuit 40. Processing circuit 40 also includes ADCs 21A-21C, for receiving inputs from reference microphone R, error microphone E and near speech microphone NS, respectively. In alternative embodiments in which one or more of reference microphone R, error microphone E and near speech microphone NS have digital outputs, the corresponding ones of ADCs 21A-21C are omitted and the digital microphone signal(s) are interfaced directly to processing circuit 40. DAC 23 and amplifier A1 are also provided by processing circuit 40 for providing the speaker output signal, including anti-noise as described above. The speaker output signal may be a digital output signal for provision to a module that reproduces the digital output signal acoustically.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

at least one microphone mounted on the housing for providing at least one microphone signal indicative of the ambient audio sounds;

a delta-sigma modulator for quantizing the at least one microphone signal at an oversampled rate substantially higher than a baseband audio rate of the audio signal; and a processing circuit that generates the anti-noise signal using an adaptive filter operating at the oversampled rate to reduce the presence of the ambient audio sounds heard by the listener in conformity with the at least one microphone signal, wherein a wideband response of an output of the adaptive filter includes a first lowest-frequency image and multiple higher-frequency images at multiples of the oversampled rate, wherein the processing circuit further implements a digital low-pass filter having an input coupled to an the output of the adaptive filter to remove at least some of the higher-frequency images of the quantized microphone signal that appear in the output of the adaptive filter to reduce the dynamic range required by the output of the adaptive filter, and wherein the digital low-pass filter has a corner frequency greater than a maximum frequency of an the first lowest-frequency image in the output of the adaptive filter.

2. The personal audio device of claim 1, wherein the at least one microphone is a reference microphone for providing a reference microphone signal indicative of the ambient audio sounds, and wherein the adaptive filter generates the anti-noise signal from the reference microphone signal, and wherein the output of the adaptive filter is the anti-noise signal.

3. The personal audio device of claim 2, further comprising an oversampling digital-to-analog converter having an input coupled to an output of the adaptive filter and an output coupled to the transducer for generating the audio signal.

4. The personal audio device of claim 1, wherein the at least one microphone is an error microphone mounted on the housing proximate to the transducer for providing an error microphone signal indicative of the ambient audio sounds and the acoustic output of the transducer, and wherein the adaptive filter filters the source audio to simulate an acoustic path from the transducer through the error microphone, and wherein the processing circuit further combines an output of the adaptive filter with the error microphone signal to remove components of the source audio from the error microphone signal to generate an error signal.

5. The personal audio device of claim 1, wherein the at least one microphone is a reference microphone for providing a reference microphone signal indicative of the ambient audio sounds, wherein the adaptive filter filters the source audio to simulate an acoustic path from the transducer through the reference microphone, and wherein the processing circuit further combines an output of the adaptive filter with the reference microphone signal to remove components of the source audio from the reference microphone signal to generate a leakage corrected reference microphone signal.

6. The personal audio device of claim 1, wherein the digital low-pass filter is a first-order filter.

7. The personal audio device of claim 1, further comprising a gain block coupled in series with an input of the adaptive filter for applying a gain to the input of the adaptive filter, whereby an adaptive gain of the adaptive filter is decreased in operation by a magnitude of the gain.

8. The personal audio device of claim 1, wherein the digital low-pass filter removes images of the quantized at least one microphone signal that appear in the output of the adaptive filter, to prevent clipping that would otherwise occur.

9. A method of countering effects of ambient audio sounds by a personal audio device, the method comprising:

adaptively generating an anti-noise signal using an adaptive filter operating at an oversampled rate to reduce the presence of the ambient audio sounds heard by a listener in conformity with at least one microphone signal, wherein a wideband response of an output of the adaptive filter includes a first lowest-frequency image and multiple higher-frequency images at multiples of the oversampled rate;

combining the anti-noise signal with source audio;

providing a result of the combining to a transducer at a baseband audio rate substantially lower than the oversampled rate of the adaptive filter;

measuring the ambient audio sounds with at least one microphone to produce at least one microphone signal indicative of the ambient audio sounds;

quantizing the at least one microphone signal at the oversampled rate with a delta-sigma modulator; and filtering the anti-noise signal with a digital low-pass filter to remove at least some of the higher-frequency images of the quantized microphone signal that appear in the output of the adaptive filter to reduce the dynamic range required by the output of the adaptive filter, wherein the digital low-pass filter has a corner frequency greater than a maximum frequency of the first lowest-frequency image in the output of the adaptive filter.

10. The method of claim 9, wherein the at least one microphone is a reference microphone for providing a reference microphone signal indicative of the ambient audio sounds, and wherein the adaptively generating generates the anti-noise signal from the reference microphone signal, and wherein the filtering filters the anti-noise signal.

11. The method of claim 10, further comprising generating the audio signal with an oversampling digital-to-analog converter having an input coupled to an output of the adaptive filter and an output coupled to the transducer.

12. The method of claim 9, wherein the at least one microphone signal is an error microphone signal indicative of the ambient audio sounds and the acoustic output of the transducer, wherein the adaptive filter filters the source audio to simulate an acoustic path from the transducer through the error microphone, and wherein the method further comprises combining an output of the adaptive filter with the error microphone signal to remove components of the source audio from the error microphone signal to generate an error signal.

13. The method of claim 9, wherein the at least one microphone is a reference microphone for providing a reference microphone signal indicative of the ambient audio sounds, wherein the adaptive filter filters the source audio to simulate an acoustic path from the transducer through the reference microphone, and wherein the method further comprises combining an output of the adaptive filter with the reference microphone signal to remove components of the source audio from the reference microphone signal to generate a leakage corrected reference microphone signal.

14. The method of claim 9, wherein the digital low-pass filter is a first-order filter.

15. The method of claim 9, further comprising applying a gain to the input of the adaptive filter, whereby an adaptive gain of the adaptive filter is decreased in operation by a magnitude of the gain.

16. The method of claim 9, wherein the filtering removes images of the quantized at least one microphone signal that appear in the output of the adaptive filter, to prevent clipping that would otherwise occur.

17. An integrated circuit for implementing at least a portion of a personal audio device, comprising:

an output for providing an output signal to an output transducer including both source audio for playback to a listener and an anti-noise signal for countering the effects of ambient audio sounds in an acoustic output of the transducer;

at least one microphone input for receiving at least one microphone signal indicative of the ambient audio sounds;

a delta-sigma modulator for quantizing the at least one microphone signal at an oversampled rate substantially higher than a baseband audio rate of the audio signal; and a processing circuit that adaptively generates the anti-noise signal using an adaptive filter operating at the oversampled rate to reduce the presence of the ambient audio sounds heard by the listener in conformity with the at least one microphone signal, wherein a wideband response of an output of the adaptive filter includes a first lowest-frequency image and multiple higher-frequency images at multiples of the oversampled rate, wherein the processing circuit further implements a digital low-pass filter having an input coupled to the output of the adaptive filter to remove at least some of the higher-frequency images of the quantized microphone signal that appear in the output of the adaptive filter to reduce the dynamic range required by the output of the adaptive filter, and wherein the digital low-pass filter has a corner frequency greater than a maximum frequency of an the first lowest-frequency image in the output of the adaptive filter.

18. The integrated circuit of claim 17, wherein the at least one microphone is a reference microphone for providing a reference microphone signal indicative of the ambient audio sounds, and wherein the adaptive filter generates the anti-noise signal from the reference microphone signal, and wherein the output of the adaptive filter is the anti-noise signal.

19. The integrated circuit of claim 18, further comprising an oversampling digital-to-analog converter having an input coupled to an output of the adaptive filter and an output coupled to the transducer for generating the audio signal.

20. The integrated circuit of claim 17, wherein the at least one microphone signal is an error microphone signal indicative of the ambient audio sounds and the acoustic output of the transducer, and wherein the adaptive filter filters the source audio to simulate an acoustic path from the transducer through the error microphone and wherein the processing circuit further combines an output of the adaptive filter with the error microphone signal to remove components of the source audio from the error microphone signal to generate an error signal.

21. The integrated circuit of claim 17, wherein the at least one microphone signal is a reference microphone signal indicative of the ambient audio sounds, wherein the adaptive filter filters the source audio to simulate an acoustic path from the transducer through the reference microphone, and wherein the processing circuit further combines an output of the adaptive filter with the reference microphone signal to remove components of the source audio from the reference microphone signal to generate a leakage corrected reference microphone signal.

22. The integrated circuit of claim 17, wherein the digital low-pass filter is a first-order filter.

23. The integrated circuit of claim 17, further comprising a gain block coupled in series with an input of the adaptive filter for applying a gain to the input of the adaptive filter, whereby an adaptive gain of the adaptive filter is decreased in operation by a magnitude of the gain.

24. The integrated circuit of claim 17, wherein the digital low-pass filter removes images of the quantized at least one microphone signal that appear in the output of the adaptive filter, to prevent clipping that would otherwise occur.

* * * * *